(12) United States Patent
Pajunk et al.

(10) Patent No.: US 7,194,312 B2
(45) Date of Patent: Mar. 20, 2007

(54) TENSION ADAPTER FOR A CATHETER

(76) Inventors: Heinrich Pajunk, Am Holzplatz 5-7, D-78187 Geisingen (DE); Horst Pajunk, Am Holzplatz 5-7, D-78187 Geisingen (DE)

( * ) Notice: Subject to any disclaimer, the term of this patent is extended or adjusted under 35 U.S.C. 154(b) by 474 days.

(21) Appl. No.: 10/221,437

(22) PCT Filed: Jan. 5, 2002

(86) PCT No.: PCT/EP02/00048

§ 371 (c)(1),
(2), (4) Date: Jan. 6, 2003

(87) PCT Pub. No.: WO02/062417

PCT Pub. Date: Aug. 15, 2002

(65) Prior Publication Data

US 2003/0181892 A1 Sep. 25, 2003

(30) Foreign Application Priority Data

Jan. 11, 2001 (DE) ............................. 101 00 975

(51) Int. Cl.
*A61N 1/18* (2006.01)
(52) U.S. Cl. ...................................................... 607/37
(58) Field of Classification Search ................ 604/533, 604/536; 606/1; 607/37
See application file for complete search history.

(56) References Cited

U.S. PATENT DOCUMENTS

| 3,367,339 A | 2/1968 | Sessions |
| 4,096,860 A * | 6/1978 | McLaughlin ................. 604/44 |
| 4,142,532 A | 3/1979 | Ware .......................... 128/419 |
| 4,226,244 A | 10/1980 | Coury et al. ................. 128/419 |
| 5,007,902 A | 4/1991 | Witt ............................. 604/117 |
| 5,211,637 A | 5/1993 | Goto et al. .................. 604/283 |
| 5,507,732 A * | 4/1996 | McClure et al. ............. 604/533 |
| 5,509,911 A * | 4/1996 | Cottone et al. ............. 604/536 |
| 5,620,426 A * | 4/1997 | Braithwaite ................. 604/533 |
| 5,800,407 A | 9/1998 | Eldor .......................... 604/264 |
| 5,891,100 A * | 4/1999 | Fleckenstein ............... 604/175 |

FOREIGN PATENT DOCUMENTS

| DE | EP 0 596 344 | 10/1993 |
| DE | 198 43 427 | 9/1998 |
| DE | GB 2 331 339 | 10/1998 |
| EP | 0 608 985 | 2/1997 |

OTHER PUBLICATIONS

Polymedic Stimcath. Stimcath monopolar.

* cited by examiner

*Primary Examiner*—George Manuel
*Assistant Examiner*—Lenwood Faulcon, Jr.
(74) *Attorney, Agent, or Firm*—O'Shea, Getz & Kosakowski, P.C.

(57) ABSTRACT

A tension adapter for a catheter is disclosed, in which a wire is arranged for electrical stimulation. The tension adapter tensions the catheter by means of a hollow cylindrical elastic tensioning piece (26) which is axially flattened. A contact lug (24) is proximally connected to the tensioning piece (26), into which the proximal end of the catheter extends, whereby the outwardly-bent wire on the catheter comes into contact with the contact lug (24). The contact lug (24) comprises an electrical lead running to the exterior.

15 Claims, 3 Drawing Sheets

TENSION ADAPTER FOR A CATHETER

The invention relates to a clamp adapter for a catheter according to the preamble of Claim 1.

In anesthesia, for lengthy operations, postoperative pain therapy, and treatment of chronic pain states, the nerves supplying a specific region of the body are blocked by an anesthetic. A catheter is used to introduce the anesthetic or other liquid and its distal end is positioned as close as possible to the nerve to achieve an optimum effect with a minimum quantity of anesthetic. In order for the catheter to be placed in the desired location and remain in position for a long time if necessary, it consists of a long, thin, flexible plastic tube.

For insertion of the flexible catheter into the sheath or canal of the nerve, a cannula is used which is inserted into the sheath or canal of the nerve, through which cannula the catheter is inserted. In order to apply a liquid, for example an anesthetic, through the catheter, a syringe is attached to the proximal end of the catheter that is still outside the body. An adapter fitted to the proximal end of the catheter is used for this purpose. If the catheter is to remain in position for a lengthy period of time, the cannula serving to introduce the catheter must be withdrawn. In doing so it is necessary to remove the adapter from the catheter so that the cannula can be pulled away at the proximal end of the catheter. In order to add further anesthetic through the catheter that is in position after the cannula is removed the adapter must be re-attached to the end of the catheter. In order to mount the adapter simply and removably at the end of the catheter, the use of a clamp adapter of the species referred to at the outset is known. This clamp adapter contains a hollow cylindrical clamping part made of a soft elastic material. The proximal end of the catheter is fed coaxially into this clamping part. Then the clamping part is upset axially, reducing its internal diameter and fixing the catheter and sealing it at its external circumference.

In order to place the distal end of the catheter as precisely as possible, it is known to design the catheter for electrical stimulation of the nerve. For this purpose, a thin wire is disposed in the catheter, contacting the nerve with a smooth contact tip at the distal tip of the catheter. At the proximal end of the catheter, the wire is brought out of the catheter and connected to a stimulator. When the known clamp adapter is used, the wire must be led back externally to the catheter in front of the distal end of the clamp adapter. At this point the bare end of the wire is gripped by a clamp and makes contact. Gripping the wire with the clamp attached to the stimulator is a delicate matter. Moreover, the grip of the clamp on the wire and the contact connection of the wire by the clamp are unreliable.

The goal of the invention is to provide a clamp adapter that permits simple and reliable contacting of a catheter designed for electrical stimulation.

This goal is achieved according to the invention by a clamp adapter with the features of Claim 1.

Advantageous embodiments of the invention are described in the subclaims.

According to the invention, a contact bushing is disposed in the clamp adapter that connects proximally to the clamping part and is in a conductive connection with an externally guided electrical connection for the stimulator. If the proximal end of the catheter is introduced into the clamp adapter, the end of the wire projecting out of the proximal end of the catheter abuts the catheter externally and comes forcibly into conducting contact with the contact bushing. No measures or procedures other than those required for mounting a conventional clamp adapter are necessary in order to contact the wire for electrical stimulation. Connecting the clamp adapter to the stimulator is simple and reliable because the electrical connection is made as a plug-in connection for example.

In one advantageous embodiment, the internal bore of the contact bushing is made conical so that it tapers in the insertion direction of the catheter. Because of this conical tapering of the contact bushing, the wire abutting the catheter externally is pressed more against the inside wall of the contact bushing when the catheter is inserted so that an especially high contact pressure and an especially reliable contact result.

The invention will now be described in greater detail with reference to the embodiments shown in the drawings.

Figure 1:
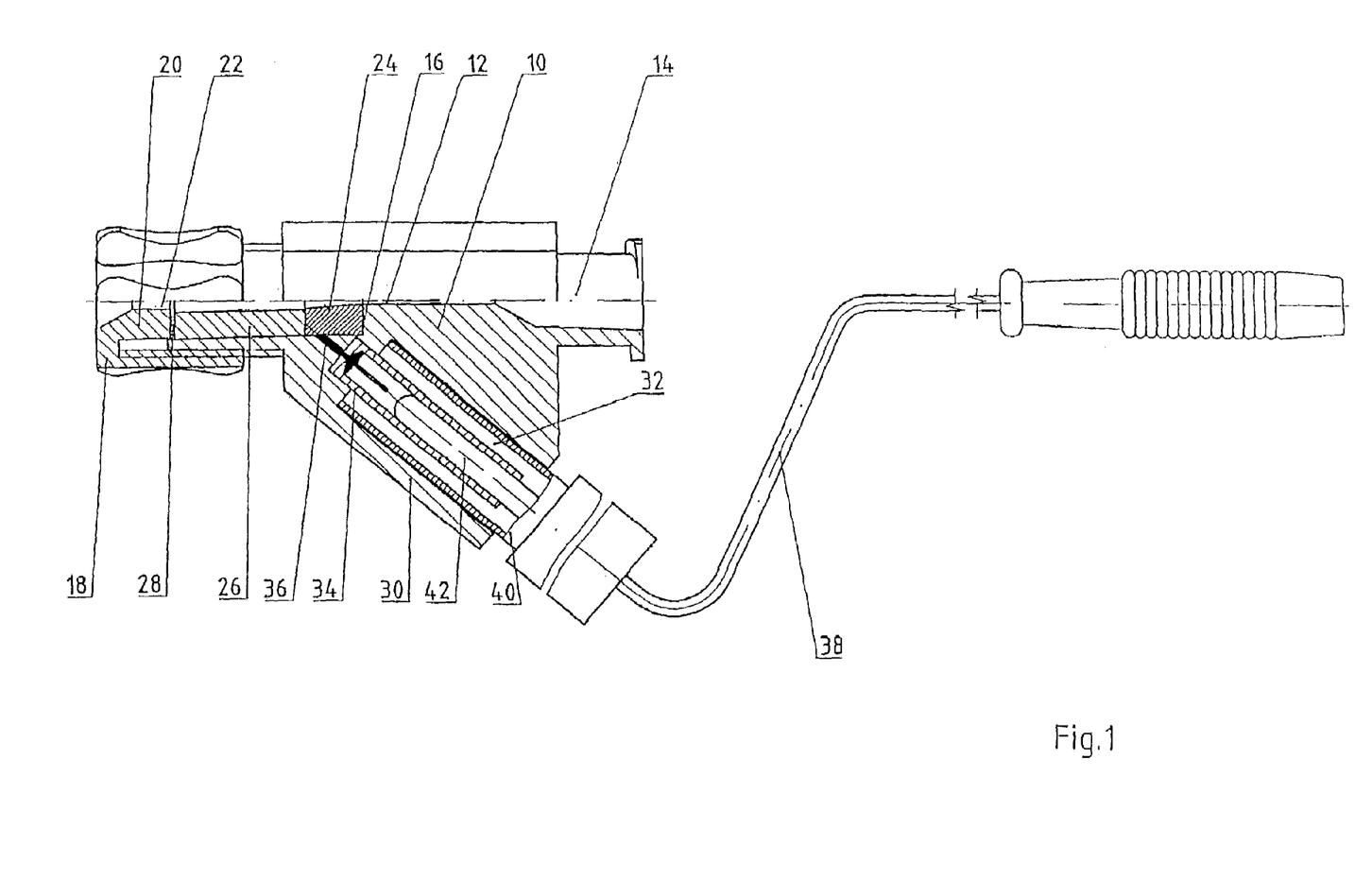
FIG. 1 is a first embodiment of the clamp adapter in axial section.
Figure 2:
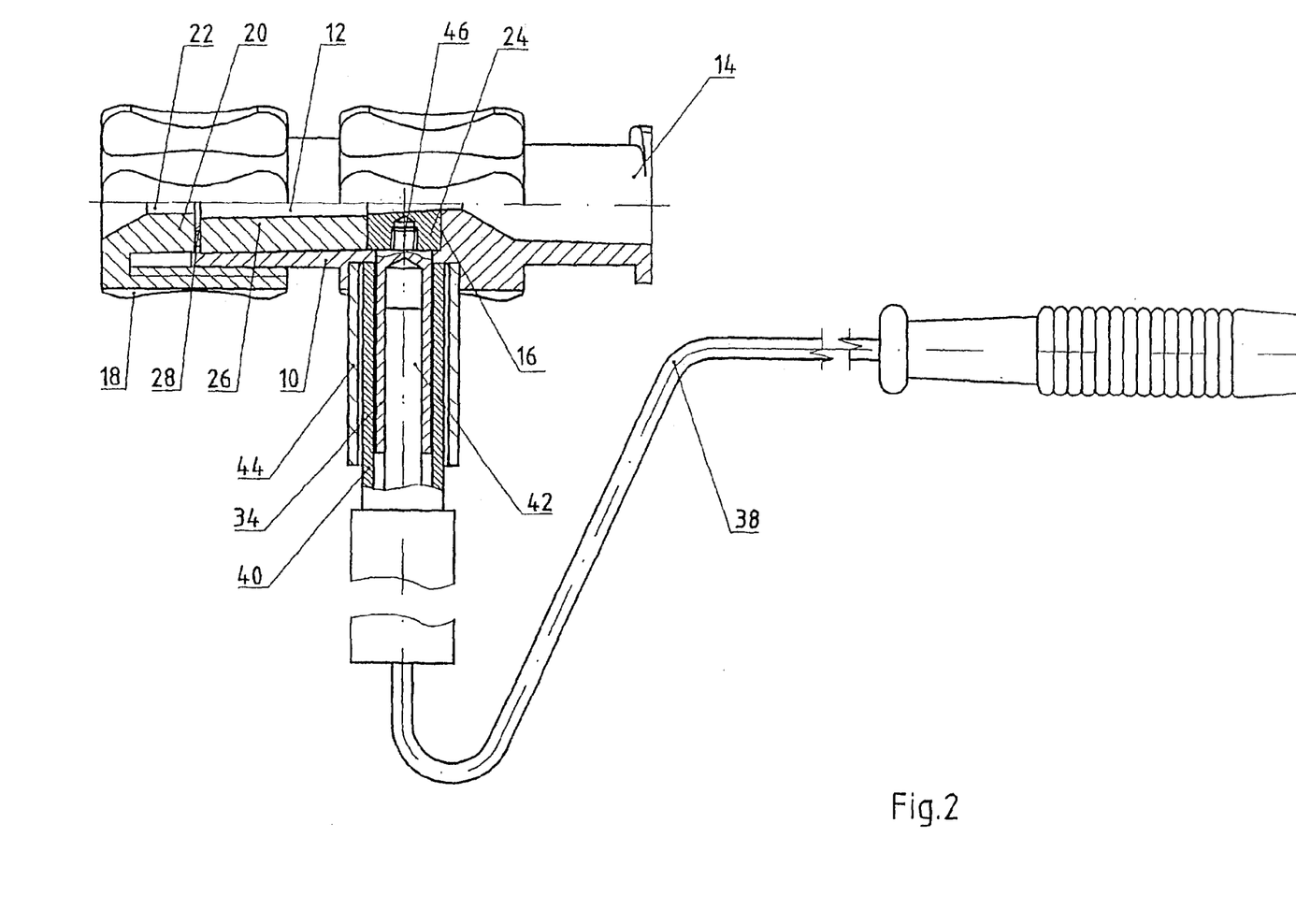
FIG. 2 is a corresponding view of a second embodiment of the clamp adapter.
Figure 3:
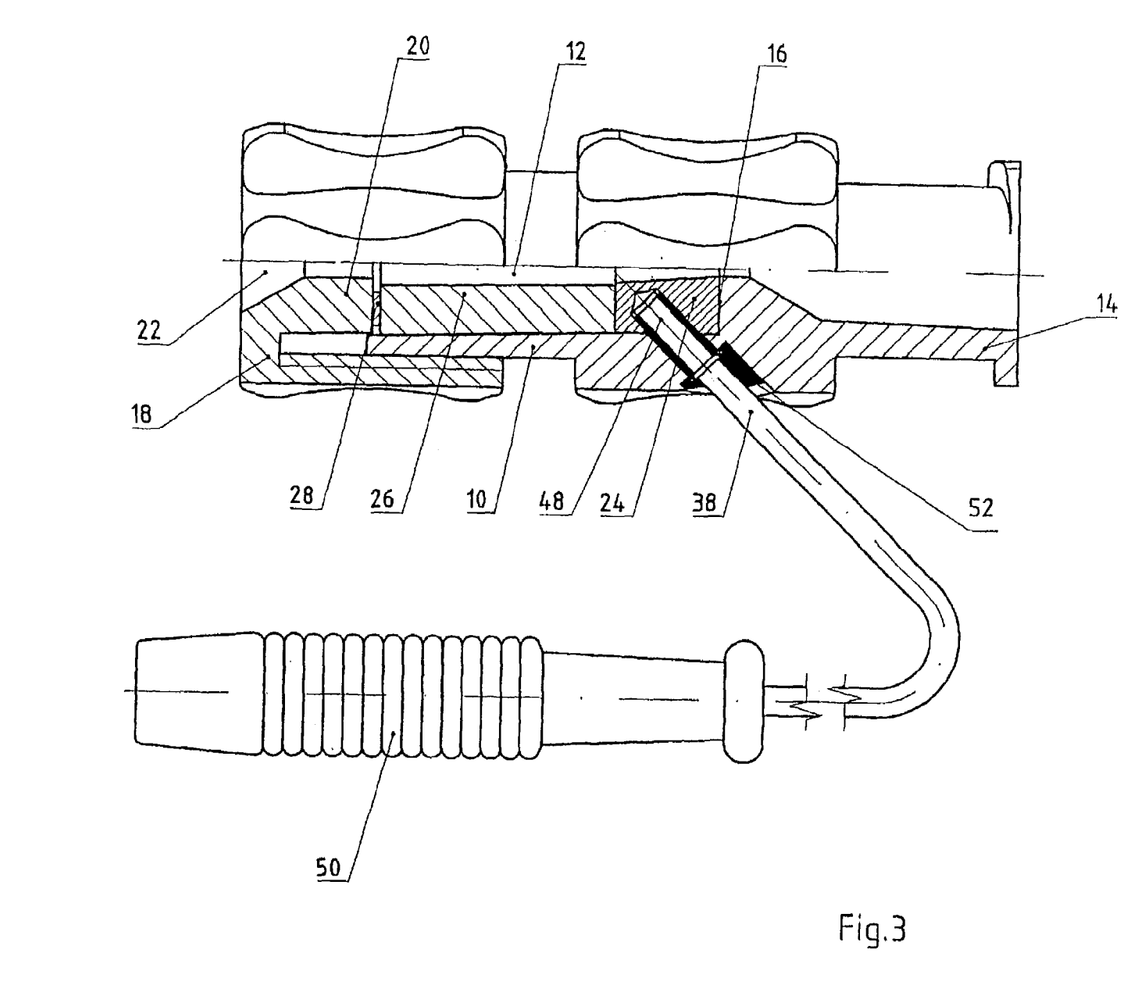
FIG. 3 is a corresponding view of a third embodiment of the clamp adapter.

In all three embodiments, the clamp adapter has a clamping body 10 made of an insulating plastic. Clamping body 10 is traversed by a bore 12 in the axial direction. At the proximal end of clamping body 10, bore 12 merges coaxially with a syringe fitting 14 that can be made in the form of a Luer lock fitting for example.

Bore 12 expands in the distal direction by a radial internal shoulder 16. Starting at internal shoulder 16, bore 12 expands slightly conically in the distal direction. At the distal end, clamping body 10 has an external thread onto which a clamping lid 18 of the union nut type with an internal thread can be screwed. The clamping lid 18 grips coaxially in bore 12 with an axially projecting hub 20. The clamping lid 18 and its hub 20 are traversed coaxially by an opening 22.

A contact bushing 24 is inserted into bore 12, said bushing having the shape of a hollow cylinder and being made of an electrically conducting material, especially a metal. Contact bushing 24 abuts internal shoulder 16 axially. The external diameter of contact bushing 24 corresponds to the internal diameter of expanded bore 12, while the internal bore of contact bushing 24 has a diameter that corresponds to the smaller diameter of bore 12 proximally to internal shoulder 16. The internal bore of contact bushing 24 tapers slightly conically in the proximal direction.

At the distal end of the contact bushing 24, a clamping part 26 is connected, which also has the shape of a hollow cylinder and is made of an elastic material, preferably an elastic plastic. The internal diameter and the external diameter of the clamping part 26 correspond to the internal diameter and the external diameter of contact bushing 24 so that clamping part 26 and contact bushing 24 abut each other smoothly as far as their internal and external diameters are concerned. Clamping part 26 can expand slightly conically in the distal direction corresponding to bore 12.

When clamping lid 18 is screwed on, its hub 20 comes to rest axially on the distal face of clamping part 26. Between hub 20 and clamping part 26 is a washer 28, preferably made of metal, so that hub 20 can turn clamping lid 18 without bringing clamping part 26 with it.

In the design described thus far, the embodiments correspond to FIGS. 1 to 3. These embodiments also correspond in terms of the insertion and clamping of the catheter, not shown.

To insert the catheter, clamping lid 18 is unscrewed in the distal direction until its hub 20 is no longer applying axial pressure to clamping part 26. The catheter is introduced from the distal side through opening 22 in clamping lid 18 and through clamping part 26 until its proximal end reaches contact bushing 24. The wire protruding from the proximal end of the catheter for electrical stimulation is thus bent radially outward over the edge of the catheter so that it bends around the proximal edge of the catheter when the catheter is pushed into the clamp adapter and externally abuts the circumference of the catheter. The internal diameter of opening 22, of clamping part 26, and of contact bushing 24 are adjusted to the external diameter of the catheter so that this catheter can be introduced easily but with a small amount of radial play. The internal bore of contact bushing 24 however tapers in the proximal direction to an internal diameter that is the same as or slightly smaller than the external diameter of the catheter. When the proximal end of the catheter enters the contact bushing 24, the wire abutting the circumference of the catheter externally is pressed by the wedge effect of the conical taper against contact bushing 24 and comes into good electrically conducting contact with contact bushing 24. Once the catheter has been inserted, the clamping lid 18 is screwed in the proximal direction so that its hub 20 penetrates into bore 12. Thus, hub 20 pushes axially against clamping part 26 through washer 28. Since the clamping part 26 is axially supported by contact bushing 24 on internal shoulder 16, this leads to an axial upset of elastic clamping part 26. This upset has the effect that clamping part 26 bulges radially and increases its wall thickness. Since clamping part 26 is unable to expand radially outward, this upsetting causes the internal diameter of clamping part 26 to diminish so that this clamping part 26 becomes firmly applied to the external circumference of the catheter. The catheter is thus clamped in the clamp adapter and held axially. A liquid, for example an anesthetic, can now be fed through bore 12 into the catheter through a syringe fitted to syringe fitting 14.

If the clamp adapter has to be removed once more from the end of the catheter, it is merely necessary to unscrew the clamping lid 18 until the clamping part 26 is unloaded axially, assumes its original shape, and releases the catheter.

For electrical stimulation, the wire running in the catheter must be placed in electrically conducting contact with a stimulator. For this purpose, contact bushing 24, with which the wire is in conducting contact, has an externally guided electrical connection through the plastic housing of clamping body 10. FIGS. 1 to 3 show different embodiments of this connection.

In the embodiment of FIG. 1, clamping body 10 has a lateral broadened area 30 whose external contour forms an angle of approximately 45°, opening in a proximal direction, with the center axis of bore 12. A plug receptacle 32 in the shape of a blind hole is formed in this broadened area 30, with the axis of said receptacle 32 also running at an angle of 45°. In plug receptacle 32, a conducting plug bushing 34 is located coaxially, which is connected at the bottom of plug receptacle 32 by a conducting pin 36 with the contact bushing 24. To connect the stimulator, not shown, there is a cable 38 connected with the stimulator which is provided with a plug 40 that can be plugged into plug receptacle 32, so that a plug pin 42 of plug 40 contacts plug bushing 34.

In the embodiment of FIG. 2, the electrical connection for the stimulator is at right angles to the axis of the clamp adapter. A radially projecting plastic tube 44 is inserted into the clamping body 10, forming the plug receptacle. The plug bushing 34 is disposed coaxially in the plastic tube 44, said bushing being screwed by a screw pin 46 into contact bushing 24. In this case as well, a connecting cable 38 is plugged by a plug 40 into the plug receptacle and into plug bushing 34.

In the embodiment of FIG. 3, a contact pin 48 is inserted into contact bushing 24 at an angle of 45° to the axis of bore 12. A cable 38 is connected to contact pin 48, while at its other end there is a plug connector 50 for connecting the stimulator. Contact pin 48 with cable 38 soldered thereto is cast in clamping body 10 or glued with an adhesive 52.

LIST OF REFERENCE SYMBOLS 10 clamping body
12 bore
14 syringe fitting
16 internal shoulder
18 clamping lid
20 hub
22 opening
24 contact bushing
26 clamping part
28 washer
30 expansion
32 plug receptacle
34 plug bushing
36 pin
38 cable
40 plug
42 plug pin
44 plastic tube
46 screw pin
48 contact pin
50 plug connector
52 adhesive

The invention claimed is:

1. A clamp adapter for a catheter, comprising a clamping body made of an insulator, a fitting bore passing axially through said clamping body, a syringe fitting located proximally to said clamping body, a hollow cylindrical elastic clamping part inserted into said bore distally and supported axially in the proximal direction, a clamping lid placed distally on said clamping body and abutting the distal face of said clamping part, the catheter being insertable through an opening of the clamping lid axially into said clamping part and being releasably clampable by said clamping part that is axially upset by said clamping lid, where to provide a contact for a wire located in the catheter for electrical stimulation in said clamping body an electrically conducting contact bushing is located proximally to the clamping part, said contact bushing having an internal bore that coaxially abuts the internal bore of said clamping part, and where said contact bushing has an electrical connection guided outward through said clamping body.

2. The clamp adapter of claim 1, where the contact bushing is located axially between an internal shoulder of said fitting bore and said clamping part and supports said clamping part axially.

3. The clamp adapter of claim 2, where the internal bore of the contact bushing tapers conically in the proximal direction.

4. The clamp adapter of claim 3, where the electrical connection has a plug connector held in a clamping body and connected electrically with said contact bushing.

5. The clamp adapter of claim 3, where the electrical connection has a cable connected in conducting fashion with said contact bushing with a plug connector at the other end of said cable.

6. A tension adapter for a catheter, comprising:
a clamping body having a distal stub shaft, an axial bore running from a proximal end to a distal end, and an external electrical connection;
an electrically conducting plug bushing mounted coaxially about said axial bore, and electrically in contact with said external electrical connection;
an elastic clamping part mounted coaxially about said axial bore and distally adjacent to said electrically conducting plug bushing to releasably clamp the catheter; and
a clamping lid that is threadingly engaged over said distal stub shaft to move axially over said distal stub shaft, and having a lid bore that is coaxial with said axial bore to receive the catheter, where said clamping lid applies an axial force to said elastic clamping part to cause radial expansion of said elastic clamping part that secures the catheter within said tension adapter.

7. The tension adapter of claim 6, where said electrically conducting plug bushing includes an internal surface that is radially adjacent to and defines a section of said axial bore, and tapers to provide a wider radius of said axial bore in the direction of said distal end in comparison to the direction of said proximal end.

8. The tension adapter of claim 6, where said electrically conducting plug bushing includes an internal surface that is radially adjacent to said axial bore, and tapers slightly conically to provide an increasingly wider radius of said axial bore from said proximal end to said distal end.

9. The tension adapter of claim 8, where said elastic clamping part comprises an elastic plastic material.

10. The tension adapter of claim 8, further comprising a washer mounted coaxial to said axial bore, and distally adjacent to said elastic clamping part and proximally adjacent to said clamping lid.

11. The tension adapter of claim 6, where said clamping body comprises a syringe fitting at said proximal end that provides a flow path into said axial bore.

12. The tension adapter of claim 9, where said clamping body is formed from an insulating plastic.

13. A tension adapter for a catheter, comprising:
an electrically nonconductive housing having a distal stub shaft, an axial bore running from a proximal end to a distal end, and an external electrical connection that is connected to a conducting pin within said housing;
an electrically conductive bushing mounted coaxially about said axial bore, and electrically in contact with said conducting pin;
an elastic clamping part mounted coaxially about said axial bore and distally adjacent to said electrically conductive bushing to releasably clamp the catheter; and
a clamping lid that moves axially along said distal stub shaft, and having a lid bore that is coaxial with said axial bore, where said clamping lid applies an axial force to said elastic clamping part causing radial expansion of said elastic clamping part into said axial bore to secure the catheter to said tension adapter.

14. The tension adapter of claim 13, where said electrically conductive bushing includes an internal surface that is radially adjacent to said axial bore, and tapers to provide an increasingly wider radius of said axial bore from said proximal end to said distal end.

15. The tension adapter of claim 14, further comprising a washer mounted coaxial to said axial bore, and distally adjacent to said elastic clamping part and proximally adjacent to said clamping lid.

* * * * *

UNITED STATES PATENT AND TRADEMARK OFFICE
CERTIFICATE OF CORRECTION

PATENT NO. : 7,194,312 B2
APPLICATION NO. : 10/221437
DATED : March 20, 2007
INVENTOR(S) : Pajunk et al.

It is certified that error appears in the above-identified patent and that said Letters Patent is hereby corrected as shown below:

Column 1
Line 2, insert --BACKGROUND OF THE INVENTION--
Line 3, before "invention" insert --present--
Line 3, before "a clamp" insert --to the field of catheters, and in particular to--
Line 4, delete "according to the preamble of Claim 1"
Line 7, before "blocked" insert --often--
Line 9, before "distal" delete "its" and insert --the--
Line 9, after "end" insert --of the catheter--
Line 13, delete "consists of" and insert --includes--
Line 28, delete "removed" and insert --removed,--
Line 52, delete "The goal of the invention" and insert --Therefore, there--
Line 52, delete "to provide" and insert --a need for--
Line 54, insert --SUMMARY OF THE INVENTION--
Line 55, delete "This goal is achieved according to the invention by a"
Line 56, delete "clamp adapter with features of Claim 1."
Line 57, delete "Advantageous embodiments of the invention are"
Line 58, delete "described in the subclaims."
Line 59, before "the invention" insert --an aspect of--

Column 2
Line 6, delete "advantageous"
Lines 14-15, delete "The invention will now be described in greater detail with reference to the embodiments shown in the drawings." and insert --These and other objects, features and advantages of the present invention will become more apparent in light of the following detailed description of preferred embodiments thereof, as illustrated in the accompanying drawings.--
Line 15, insert --BRIEF DESCRIPTION OF THE DRAWING--
Line 21, insert --DETAILED DESCRIPTION OF THE INVENTION--
Line 22, before "In all three", insert --Referring to FIGs. 1-3,--
Line 22, delete "In" and insert --in--
Line 23, delete "Clamping" and insert --The clamping--
Line 25, before "clamping" insert --the--
Line 25, before "bore" insert --the--
Line 28, delete "Bore" and insert --The bore--
Line 29, before "internal" insert --the--
Line 29, before "bore" insert --the--
Line 31, before "clamping" insert --the--
Line 34, before "bore" insert --the--
Line 37, before "bore" insert --the--
Line 37, delete "said" and insert --and the--
Line 38, delete "having" and insert --has--

UNITED STATES PATENT AND TRADEMARK OFFICE
CERTIFICATE OF CORRECTION

PATENT NO. : 7,194,312 B2
APPLICATION NO. : 10/221437
DATED : March 20, 2007
INVENTOR(S) : Pajunk et al.

It is certified that error appears in the above-identified patent and that said Letters Patent is hereby corrected as shown below:

Column 2 (cont'd)
Line 39, delete "Contact" and insert --The contact--
Line 40, before "internal" insert --the--
Line 41, before "contact" insert --the--
Line 42, before "expanded" insert --the--
Line 43, before "contact" insert --the--
Line 44, before "bore" insert --the--
Line 44, before "internal" insert --the--
Line 45, before "contact" insert --the--
Line 52, before "contact" insert --the--
Line 53, before "contact" insert --the--
Line 55, delete "Clamping" and insert --The clamping--
Line 56, before "bore" insert --the--
Line 57, before "clamping" insert --the--
Line 58, before "clamping" insert --the--
Line 59, before "hub" insert --the--
Line 59, before "clamping" insert --the--
Line 60, before "hub" insert --the--
Line 60, before "clamping" insert --the--
Line 61, before "clamping" insert --the--
Line 66, before "clamping" insert --the--

Column 3
Line 1, before "clamping" insert --the--
Line 2, before "opening" insert --the--
Line 2, before "clamping" insert --the--
Line 3, before "clamping" insert --the--
Line 4, before "contact" insert --the--
Line 10, before "opening" insert --the--
Line 10, before "clamping" insert --the--
Line 10, before "contact" insert --the--
Line 13, before "contact" insert --the--
Line 17, before "contact" insert --the--
Line 19, before "contact" insert --the--
Line 23, before "bore" insert --the--
Line 23, before "hub" insert --the--
Line 24, before "clamping" insert --the--
Line 24, before "washer" insert --the--
Line 25, before "contact" insert --the--
Line 26, before "internal" insert --the--
Line 27, before "elastic" insert --the--

UNITED STATES PATENT AND TRADEMARK OFFICE
CERTIFICATE OF CORRECTION

PATENT NO. : 7,194,312 B2
APPLICATION NO. : 10/221437
DATED : March 20, 2007
INVENTOR(S) : Pajunk et al.

It is certified that error appears in the above-identified patent and that said Letters Patent is hereby corrected as shown below:

Column 3 (cont'd)
Line 28, before "clamping" insert --the--
Line 29, before "clamping" insert --the--
Line 31, before "clamping" insert --the--
Line 35, before "bore" insert --the--
Line 36, before "syringe" insert --the--
Line 43, before "contact" insert --the--
Line 46, before "clamping" insert --the--
Line 49, before "clamping" insert --the--
Line 52, before "bore" insert --the--
Line 54, delete "said" and insert --the--
Line 55, before "plug" insert --the--
Line 56, before "plug" insert --the--
Line 60, before "plug" insert --the--
Line 61, before "plug" insert --the--
Line 61, before "plug bushing" insert --the--
Line 66, delete "said" and insert --and the--
Line 67, delete "being" and insert --is--
Line 67, before "contact" insert --the--

Column 4
Line 2, before "plug" insert --the--
Line 5, before "contact" insert --the--
Line 5, before "bore" insert --the--
Line 6, before "contact" insert --the--
Line 8, delete "Contact" and insert --The contact--
Line 8, before "cable" insert --the--
Line 9, before "clamping" insert --the--
Line 11, delete "LIST OF REFERENCE SYMBOLS"
Line 13, delete "10 clamping body"
Line 14, delete "12 bore"
Line 15, delete "14 syringe fitting"
Line 16, delete "16 internal shoulder"
Line 17, delete "18 clamping lid"
Line 18, delete "20 hub"
Line 19, delete "22 opening"
Line 20, delete "24 contact bushing"
Line 21, delete "26 clamping part"
Line 22, delete "28 washer"
Line 23, delete "30 expansion"
Line 24, delete "32 plug receptacle"

UNITED STATES PATENT AND TRADEMARK OFFICE
CERTIFICATE OF CORRECTION

PATENT NO. : 7,194,312 B2
APPLICATION NO. : 10/221437
DATED : March 20, 2007
INVENTOR(S) : Pajunk et al.

It is certified that error appears in the above-identified patent and that said Letters Patent is hereby corrected as shown below:

Column 4 (cont'd)
Line 25, delete "34 plug bushing"
Line 26, delete "36 pin"
Line 27, delete "38 cable"
Line 28, delete "40 plug"
Line 29, delete "42 plug pin"
Line 30, delete "44 plastic tube"
Line 31, delete "46 screw pin"
Line 32, delete "48 contact pin"
Line 33, delete "50 plug connector"
Line 34, delete "52 adhesive"
Line 35, insert --Although the present invention has been shown and described with respect to several preferred embodiments thereof, various changes, omissions and additions to the form and detail thereof, may be made therein, without departing from the spirit and scope of the invention.--

Signed and Sealed this

Eighth Day of May, 2007

JON W. DUDAS
*Director of the United States Patent and Trademark Office*